United States Patent
Ogawa et al.

(10) Patent No.: US 9,504,250 B2
(45) Date of Patent: *Nov. 29, 2016

(54) ARTHROPOD PEST CONTROL COMPOSITION AND METHOD FOR CONTROLLING ARTHROPOD PESTS

(71) Applicant: SUMITOMO CHEMICAL COMPANY, LIMITED, Tokyo (JP)

(72) Inventors: Masaomi Ogawa, Kasai (JP); Yukie Hirotomi, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,791

(22) Filed: Feb. 26, 2016

(65) Prior Publication Data

US 2016/0174559 A1    Jun. 23, 2016

Related U.S. Application Data

(62) Division of application No. 14/232,057, filed as application No. PCT/JP2012/068402 on Jul. 12, 2012, now Pat. No. 9,301,531.

(30) Foreign Application Priority Data

Jul. 13, 2011    (JP) .................................. 2011-155104

(51) Int. Cl.
| | |
|---|---|
| *A01N 43/22* | (2006.01) |
| *A01N 43/56* | (2006.01) |
| *A01N 43/40* | (2006.01) |
| *A01N 43/78* | (2006.01) |
| *A01N 43/50* | (2006.01) |

(Continued)

(52) U.S. Cl.
CPC .............. *A01N 43/78* (2013.01); *A01N 43/22* (2013.01); *A01N 43/40* (2013.01); *A01N 43/50* (2013.01); *A01N 43/56* (2013.01); *A01N 43/707* (2013.01); *A01N 43/88* (2013.01); *A01N 47/44* (2013.01)

(58) Field of Classification Search
None
See application file for complete search history.

(56) References Cited

U.S. PATENT DOCUMENTS

| | | | |
|---|---|---|---|
| 4,742,060 A | 5/1988 | Shiokawa et al. | |
| 5,034,404 A | 7/1991 | Uneme et al. | |

(Continued)

FOREIGN PATENT DOCUMENTS

| | | |
|---|---|---|
| CN | 101073324 A | 11/2007 |
| CN | 101203135 A | 6/2008 |

(Continued)

OTHER PUBLICATIONS

Machine Generated English translation for DE-102007045920-A1.

(Continued)

*Primary Examiner* — Traviss C McIntosh, III
(74) *Attorney, Agent, or Firm* — Birch, Stewart, Kolasch & Birch, LLP

(57) ABSTRACT

Disclosed is an arthropod pest control composition having an excellent controlling effect on arthropod pests, which comprises an amide compound represented by formula (a):

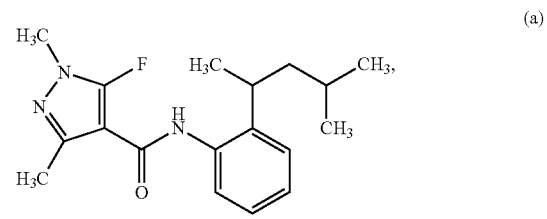

(a)

a spinosin compound represented by formula (1):

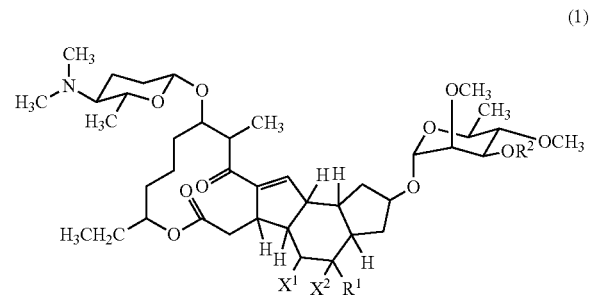

(1)

wherein $R^1$ represents a hydrogen atom or a C1-C4 alkyl group, $R^2$ represents a C1-C4 alkyl group, and $X^1$ and $X^2$ each represents a hydrogen atom, or $X^1$ and $X^2$ are taken together to form a single bond, and
one or more compounds selected from Group (A):
Group (A): the group consisting of fipronil, pymetrozine, a compound represented by formula (b):

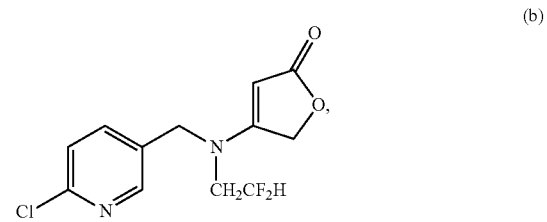

(b)

and a neonicotinoid compound containing a nitroguanidine structure.

9 Claims, No Drawings

(51) Int. Cl.
*A01N 43/707* (2006.01)
*A01N 43/88* (2006.01)
*A01N 47/44* (2006.01)

(56) References Cited

U.S. PATENT DOCUMENTS

| | | | |
|---|---|---|---|
| 5,434,181 | A | 7/1995 | Kodaka et al. |
| 5,852,012 | A | 12/1998 | Maienfisch et al. |
| 6,444,667 | B1 | 9/2002 | Andersch et al. |
| 9,301,531 | B2 * | 4/2016 | Ogawa ................... A01N 43/22 |
| 2004/0204470 | A1 | 10/2004 | Elbe et al. |
| 2008/0293566 | A1 | 11/2008 | Suty-Heinze et al. |
| 2009/0253749 | A1 | 10/2009 | Jeschke et al. |
| 2010/0197737 | A1 | 8/2010 | Hungenberg et al. |
| 2010/0298137 | A1 | 11/2010 | Hungenberg et al. |
| 2013/0123506 | A1 | 5/2013 | Jeschke et al. |

FOREIGN PATENT DOCUMENTS

| | | |
|---|---|---|
| CN | 101466705 A | 6/2009 |
| CN | 101708000 A | 5/2010 |
| DE | 102007045920 A1 | 4/2009 |
| EP | 0375316 A1 | 6/1990 |
| JP | 61-178981 A | 8/1986 |
| JP | 3-157308 A | 7/1991 |
| JP | 6-183918 A | 7/1994 |
| JP | 7-179448 A | 7/1995 |
| JP | 2002-516258 A | 6/2002 |
| JP | 2008-539179 A | 11/2008 |
| JP | 2009-531352 A | 9/2009 |
| JP | 2010-534625 A | 11/2010 |
| JP | 2011-501733 A | 1/2011 |
| WO | WO 97/00265 A1 | 1/1997 |
| WO | WO 03/010149 A1 | 2/2003 |
| WO | WO 2006/114212 A2 | 11/2006 |
| WO | WO 2007/112847 A2 | 10/2007 |
| WO | WO 2007/115644 A1 | 10/2007 |
| WO | WO 2009/015763 A1 | 2/2009 |
| WO | WO 2009/043442 A1 | 4/2009 |
| WO | WO 2010/000790 A1 | 1/2010 |
| WO | WO2010/052129 * | 5/2010 |
| WO | WO 2010/052129 A2 | 5/2010 |
| WO | WO 2010/092032 A1 | 8/2010 |
| WO | WO 2010/092119 A1 | 8/2010 |

OTHER PUBLICATIONS

The Extended European Search Report, dated Jan. 27, 2015, issued in the corresponding European Patent Application No. 12811430.3.
The First Office Action (including an English translation), dated Nov. 2, 2014, issued in the corresponding Chinese Patent Application No. 201280032593.9.
The International Preliminary Report on Patentability, dated Jan. 14, 2014, issued in the International Application No. PCT/JP2012/068402.
The Office Action (including an English translation), dated Feb. 17, 2015, issued in the corresponding Japanese Patent Application No. 2011-155104.
The Pesticide Manual, 15th Edition, Published by BCPC, ISBN 978-1-901396-18-8 (9 pages).
The Second Office Action (including an English translation), dated Jun. 2, 2015, issued in the corresponding Chinese Patent Application No. 201280032593.9.
The Written Opinion of the International Searching Authority, dated Sep. 11, 2012, issued in the International Application No. PCT/JP2012/068402.
XP-002734489: Database WPI Week 200828 Thomson Scientific, London, GB, Nov. 21, 2007; AN 2008-D86053.
XP-002734490: Database WPI Week 201038 Thomson Scientific, London, GB, May 19, 2010; AN 2010-F97344.

* cited by examiner

ARTHROPOD PEST CONTROL COMPOSITION AND METHOD FOR CONTROLLING ARTHROPOD PESTS

CROSS-REFERENCE TO RELATED APPLICATIONS

This application is a Divisional of co-pending application Ser. No. 14/232,057 filed on Jan. 10, 2014, which is a National Phase of PCT International Application No. PCT/JP2012/068402 filed on Jul. 12, 2012, which claims priority under 35 U.S.C. §119(a) to Patent Application No. 2011-155104 filed in Japan on Jul. 13, 2011. All of the above applications are hereby expressly incorporated by reference into the present application.

TECHNICAL FIELD

The present invention relates to an arthropod pest control composition and a method for controlling arthropod pests.

BACKGROUND ART

Heretofore, various compounds are known as active ingredients in arthropod pest control compositions (see, for example, The Pesticide Manual-15th edition (published by BCPC); ISBN 978-1-901396-18-8).

SUMMARY OF INVENTION

Technical Problem

An object of the present invention is to provide an arthropod pest control composition having an excellent control effect on arthropod pests.

Solution to Problem

The present inventors have intensively studied for providing an arthropod pest control composition having an excellent control effect on arthropod pests, and finally found that a composition comprising an amide compound represented by the following formula (a), a spinosin compound represented by the following formula (1) and one or more compounds selected from Group (A) has an excellent control effect on arthropod pests, thereby attaining the present invention.

Namely, the present invention includes the followings [1] to [10]:

[1] An arthropod pest control composition comprising an amide compound represented by formula (a):

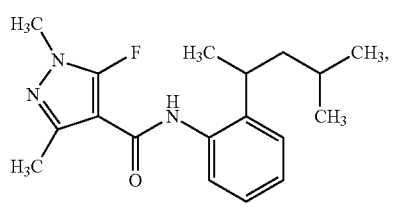

(a)

a spinosin compound represented by formula (1):

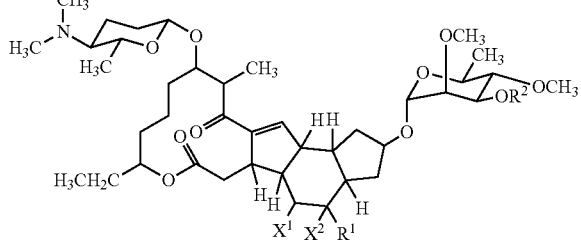

(1)

wherein $R^1$ represents a hydrogen atom or a C1-C4 alkyl group, $R^2$ represents a C1-C4 alkyl group, and $X^1$ and $X^2$ each represents a hydrogen atom, or $X^1$ and $X^2$ are taken together to form a single bond, and
one or more compounds selected from Group (A):
Group (A): the group consisting of fipronil, pymetrozine, a compound represented by formula (b):

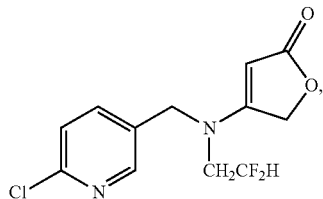

(b)

and a neonicotinoid compound containing a nitroguanidine structure.

[2] The arthropod pest control composition according to the above [1], wherein the weight ratio of the amide compound to the spinosin compound is from 50:1 to 1:50.

[3] The arthropod pest control composition according to the above [2], wherein the weight ratio of the amide compound to the one or more compounds selected from Group (A) is from 50:1 to 1:100.

[4] The arthropod pest control composition according to any one of the above [1] to [3], wherein the neonicotinoid compound is a compound represented by formula (2):

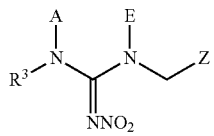

(2)

wherein $R^3$ represents a hydrogen atom or a methyl group, A and E each represents a hydrogen atom, or A and E are taken together to form $CH_2-CH_2$ or $CH_2-O-CH_2$,
Z represents a 2-chloro-5-thiazolyl group, a 6-chloro-3-pyridyl group or a 3-tetrahydrofuryl group.

[5] The arthropod pest control composition according to any one of the above [1] to [3], wherein the neonicotinoid compound is clothianidin, imidacloprid, thiamethoxam or dinotefuran.

[6] The arthropod pest control composition according to any one of the above [1] to [3], wherein the one or more compounds selected from Group (A) is pymetrozine, dinotefuran or the compound represented by formula (b).

[7] The arthropod pest control composition according to any one of the above [1] to [6], wherein the spinosin compound is spinosad or spinetoram.
[8] A method for controlling an arthropod pest, which comprises applying an effective amount of the arthropod pest control composition according to any one of the above [1] to [7] to a plant or an area in which a plant is grown.
[9] The method for controlling an arthropod pest according to the above [8], wherein the plant or the area in which a plant is grown is rice or area in which rice is grown.
[10] Use of a composition comprising the amide compound represented by formula (a), the spinosin compound represented by formula (1), and the one or more compounds selected from Group (A), as an arthropod pest control agent.

Effects of Invention

According to the present invention, it is possible to control an arthropod pest.

DESCRIPTION OF EMBODIMENTS

The arthropod pest control composition of the present invention comprises an amide compound represented by formula (a) (hereinafter sometimes referred to as "the present amide compound"):

(a)

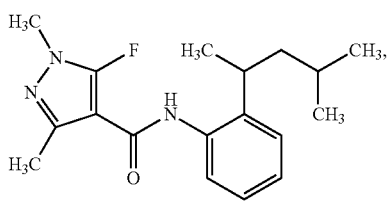

a spinosin compound represented by formula (1) (hereinafter sometimes referred to as "the present spinosin compound"):

(1)

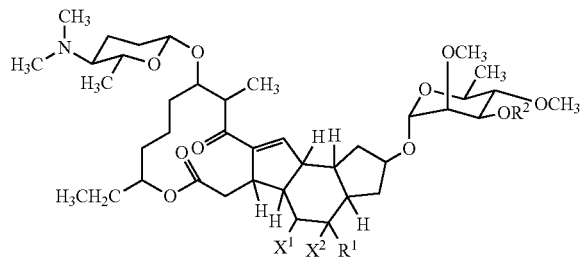

wherein $R^1$, $R^2$, $X^1$ and $X^2$ are defined as above, and one or more compounds (hereinafter sometimes referred to as "the present compound (A)") selected from the following Group (A):

Group (A): the group consisting of fipronil, pymetrozine, a compound represented by formula (b):

(b)

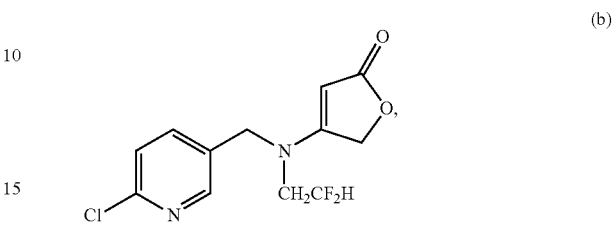

(hereinafter referred to as "the present compound (b)"), and a neonicotinoid compound containing a nitroguanidine structure (hereinafter referred to as "the present neonicotinoid compound").

The present amide compound is known and can be prepared, for example, by a process described in WO 2003/010149.

The present spinosin compound is described in, for example, EP-A-375316 and WO97/00265, and can be prepared by a process described in the documents.

In the formula (1), the "C1-C4 alkyl group" represented by $R^1$ and $R^2$ includes, for example, a methyl group and an ethyl group.

The spinosin compound represented by formula (1) wherein $X^1$ and $X^2$ are taken together to form a single bond is a compound represented by the following formula:

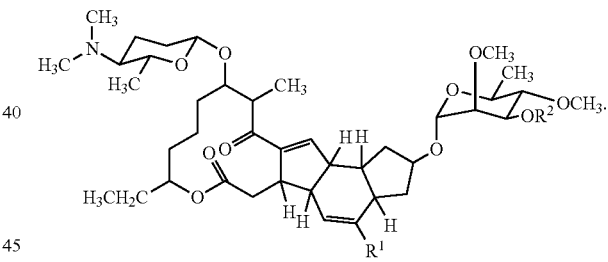

Specific examples of the present spinosin compound include spinosin A, spinosin D, spinetoram J and spinetoram L, as described below:

Spinosin A

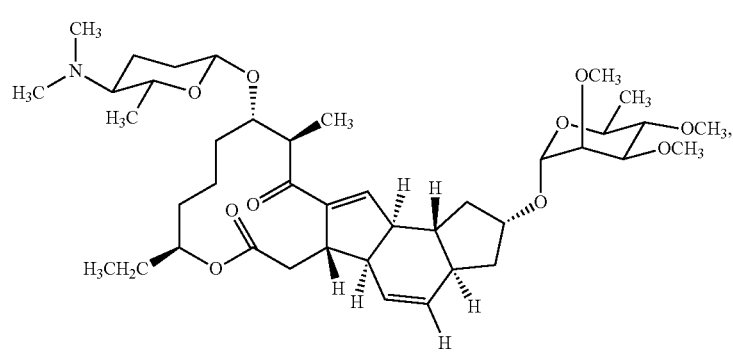

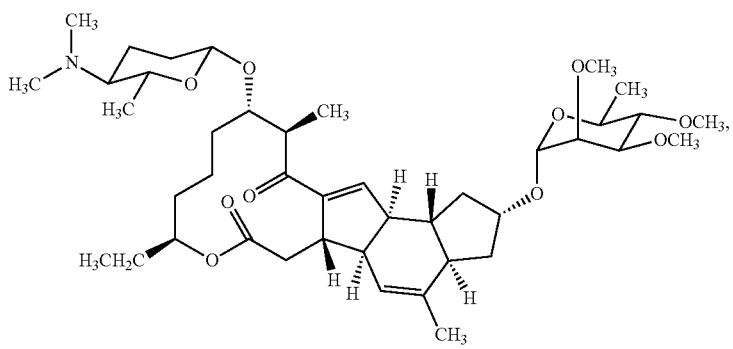

Spinosin D

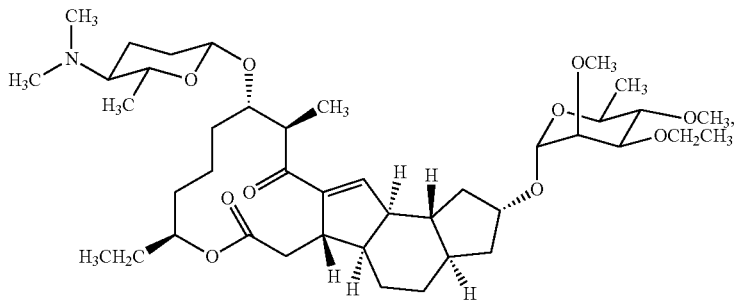

Spinosin J

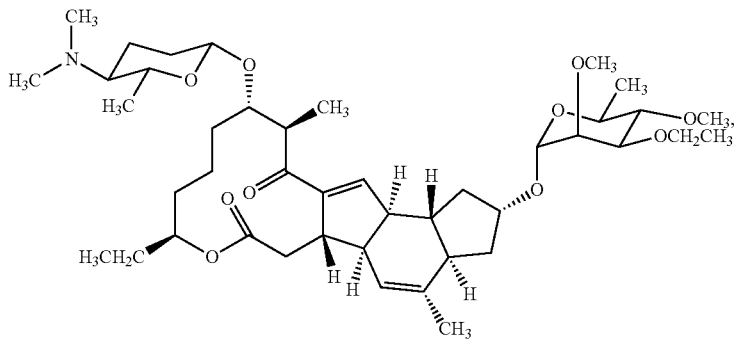

Spinosin L

A mixture of spinosyn A and spinosyn D is known by the general name "spinosad", and known as an active ingredient of a pesticide. A mixture of spinetoram J and spinetoram L is known by the general name "spinetoram", and known as an active ingredient of a pesticide. Spinosad or spinetoram can be also used in the present invention.

In spinosad, the mixing weight ratio of spinosyn A to spinosyn D is usually 50:50 to 95:5, preferably 70:30 to 95:5.

In spinetoram, the mixing weight ratio of spinetoram J to spinetoram L is usually 50:50 to 90:10, preferably 70:30 to 90:10.

Spinosad and spinetoram are both known compounds, as described in, for example, at pages 1040 and 1042 of "The Pesticide Manual-15th edition (published by BCPC); ISBN 978-1-901396-18-8". These compounds can be obtained from commercial sources or produced by a known method.

Fipronil and pymetrozine to be used in the present invention are both known compounds, as described in, for example, at pages 500 and 968 of "The Pesticide Manual-15th edition (published by BCPC); ISBN 978-1-901396-18-8". These compounds can be obtained from commercial sources or produced by a known method.

The present compound (b) is described in, for example, WO2007/115644, and can be prepared by a process described in the document.

The present neonicotinoid compound is a neonicotinoid compound containing a nitroguanidine structure, and examples thereof include a compound represented by formula (2):

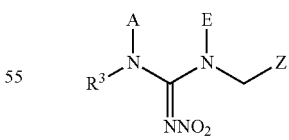

(2)

wherein $R^3$ represents a hydrogen atom or a methyl group, A and E each represents a hydrogen atom, or A and E are taken together to form $CH_2-CH_2$ or $CH_2-O-CH_2$.

Z represents a 2-chloro-5-thiazolyl group, a 6-chloro-3-pyridyl group or a 3-tetrahydrofuryl group.

The above compound represented by formula (2) is a known compound, and can be prepared, for example, by a process described in JP-A-3-157308, JP-A-61-178981, JP-A-6-183918 or JP-A-7-179448.

The compound represented by formula (2) wherein A and E are taken together to form CH₂—CH₂ is specifically a compound represented by the following formula:

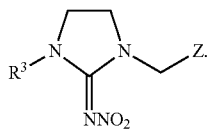

The compound represented by formula (2) wherein A and E are taken together to form CH₂—O—CH₂ is specifically a compound represented by the following formula:

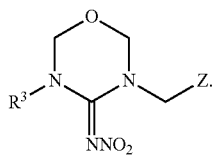

Specific examples of the present neonicotinoid compound include clothianidin, imidacloprid, thiamethoxam and dinotefuran, as follows:

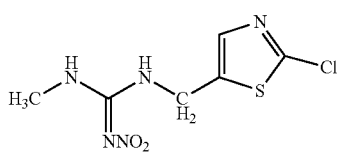
Clothianidin

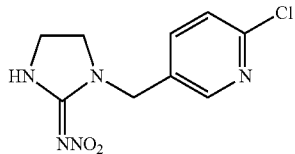
Imidacloprid

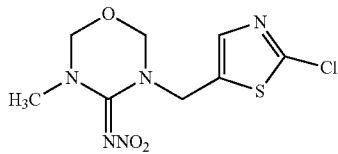
Thiamethoxam

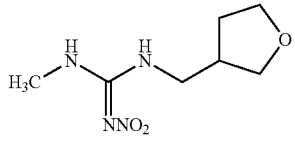
Dinotefuran

Clothianidin, imidacloprid, thiamethoxam and dinotefuran are known compounds, and are described, for example, at pages 229, 645, 1112 and 391 of "The Pesticide Manual-15th edition (published by BCPC); ISBN 978-1-901396-18-8". These compounds can be obtained from commercial sources or produced by a known method.

In the arthropod pest control composition of the present invention, the weight ratio of the present amide compound, the present spinosin compound and the present compound (A) is not particularly limited. However, the present spinosin compound is generally 0.2 to 50000 parts by weight, preferably 2 to 5000 parts by weight, more preferably 10 to 100 parts by weight, further preferably 20 to 80 parts by weight, relative to 100 parts by weight of the present amide compound. The present compound (A) is generally 0.2 to 100000 parts by weight, preferably 2 to 10000 parts by weight, more preferably 50 to 200 parts by weight, further preferably 80 to 180 parts by weight, relative to 100 parts by weight of the present amide compound. Namely, (i) the weight ratio of the present amide compound to the present spinosin compound is generally 500:1 to 1:500, preferably 50:1 to 1:50, more preferably 10:1 of 1:1, further preferably 5:1 to 1:0.8; (ii) the weight ratio of the present amide compound to the present compound (A) is generally 500:1 to 1:1000, preferably 50:1 to 1:100, more preferably 2:1 to 1:2, further preferably 1.25:1 to 1:1.8; and (iii) the weight ratio of the present amide compound to the present spinosin compound to the present compound (A) may be represented by a combination of the above weight ratio of the present amide compound to the present spinosin compound and the above weight ratio of the present amide compound to the present compound (A).

The arthropod pest control composition of the present invention may be prepared by simply mixing the present amide compound, the present spinosin compound and the present compound (A), but generally by mixing the present amide compound, the present spinosin compound and the present compound (A) and an inert carrier, and if necessary, a surfactant and/or other formulation additives, and then formulating the mixture into a formulation such as oil solution, emulsifiable concentrate, suspension concentrate, wettable powders, water dispersible granules, dusts, and granules.

Thus formulated arthropod pest control composition may be used directly, or after the addition of other inert ingredients, as an arthropod pest control agent.

The total amount of the present amide compound, the present spinosin compound and the present compound (A) in the arthropod pest control composition of the present invention is generally 0.01 to 99% by weight, preferably 0.1 to 90% by weight, more preferably 0.5 to 70% by weight.

Examples of the solid carrier used for formulation of the arthropod pest control composition include fine powders or granules of minerals (e.g., kaolin clay, attapulgite clay, bentonite, montmorillonite, acidic white clay, pyrophylite, talc, diatomaceous earth, and calicite), natural organic substances (e.g., corncob flour, and walnut shell flour), synthetic organic substances (e.g., urea), salts (e.g., calcium carbonate, and ammonium sulfate), and synthetic inorganic substances (e.g., synthetic hydrated silicon oxide).

Examples of the liquid carrier include aromatic hydrocarbons (e.g., xylene, alkylbenzene, and methyl naphthalene), alcohols (e.g., 2-propanol, ethylene glycol, propylene glycol, and ethylene glycol monoethyl ether), ketones (e.g., acetone, cyclohexanone, and isophorone), vegetable oils (e.g., soybean oil, and cotton oil), petroleum-based aliphatic hydrocarbons, esters, dimethylsulfoxide, acetonitrile, and water.

Examples of the surfactant include anionic surfactants (e.g., alkyl sulfate ester salts, alkylaryl sulfonates, dialkyl sulfosuccinates, polyoxyethylene alkylaryl ether phosphate ester salts, ligninsulfonates, and naphthalene sulfonate formaldehyde polycondensates), nonionic surfactants (e.g., polyoxyethylene alkylaryl ethers, polyoxyethylene alkylpolyoxypropylene block copolymers, and sorbitan fatty acid esters), and cationic surfactants (e.g., alkyl trimethyl ammonium salts).

Examples of the formulation additive include water-soluble polymers (e.g., polyvinyl alcohol, and polyvinyl pyrrolidone), polysaccharides [e.g., gum arabic, alginic acid and a salt thereof, CMC (carboxymethyl cellulose), and xanthane gum], inorganic substances (e.g., aluminum magnesium silicate, and alumina-sol), preservatives, colorants, and stabilizers [e.g. PAP (isopropyl acid phosphate), and BHT].

The arthropod pest control composition of the present invention may be also prepared by formulating each of the present amide compound, the present spinosin compound and the present compound (A) according to a method described above; and diluting with water, if necessary; and mixing a formulation containing the present amide compound, a formulation containing the present spinosin compound and a formulation containing the present compound (A) or dilutions thereof.

The arthropod pest control composition of the present invention can be used for protecting a plant from damage due to eating or sucking by an arthropod pest.

Examples of the arthropod pest on which the arthropod pest control composition of the present invention has controlling effect include as described below:

Hemiptera:
Delphacidae such as *Laodelphax striatellus, Nilaparvata lugens, Sogatella furcifera*; Deltocephalidae such as *Nephotettix cincticeps, Nephotettix virescens, Recilia dorsalis, Empoasca onukii*; Aphididae such as *Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Eriosoma lanigerum*; Pentatomidae such as *Nezara antennata, Trigonotylus caelestialium, Graphosoma rubrolineatum, Eysarcoris lewisi, Riptortus clavetus, Leptocorisa chinensis, Eysarcoris parvus, Halyomorpha mista, Nezara viridula*, and *Lygus lineolaris*; Aleyrodidae such as *Trialeurodes vaporariorum, Bemisia tabaci, Dialeurodes citri*, and *Aleurocanthus spiniferus*; Coccoidea such as *Aonidiella aurantii, Comstockaspis perniciosa, Unaspis citri, Ceroplastes rubens, Icerya purchasi, Planococcus kraunhiae, Pseudococcus longispinis*, and *Pseudaulacaspis pentagona*; Tingidae; Cimicoidea such as *Cimex lectularius*; Psyllidae such as *Cacopsylla pyricola*; etc.

Lepidoptera:
Pyralidae such as *Chilo suppressalis, Tryporyza incertulas, Cnaphalocrocis medinalis, Notarcha derogata, Plodia interpunctella, Ostrinia furnacalis, Hellula undalis*, and *Pediasia teterrellus*; Noctuidae such as *Spodoptera litura, Spodoptera exigua, Pseudaletia separata, Sesamia inferens, Mamestra brassicae, Agrotis Ipsilon, Plusia nigrisigna, Trichoplusia ni, Thoricoplusia* spp., *Heliothis* spp., and *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxophyes honmai, Homona magnanima, Archips fuscocupreanus*, and *Cydia pomonella*; Gracillariidae such as *Caloptilia theivora*, and *Phyllonorycter ringoneella*; Carposinidae such as *Carposina niponensis*; Lyonetiidae such as *Lyonetia* spp.; Lymantriidae such as *Lymantria* spp., and *Euproctis* spp.; Yponomeutidae such as *Plutella xylostella*; Gelechiidae such as *Pectinophora gossypiella*, and *Phthorimaea operculella*; Arctiidae such as *Hyphantria cunea*; Tineidae such as *Tinea translucens*, and *Tineola bisselliella; Tuta absoluta*; etc.

Thysanoptera:
Thripidae such as *Frankliniella occidentalis, Thrips parmi, Scirtothrips dorsalis, Thrips tabaci, Frankliniella intonsa, Frankliniella fusca, Stenchaetothrips biformis, Haplothrips aculeatus*; etc.

Diptera:
Agromyzidae such as *Hylemya antiqua, Hylemya platura, Agromyza oryzae, Hydrellia griseola, Chlorops oryzae*, and *Liriomyza trifolii; Dacus cucurbitae, Ceratitis capitata*; etc.

Coleoptera:
*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne*; etc.

Orthoptera:
*Gryllotalpa africana, Oxya yezoensis, Oxya japonica*; etc.

Among the above arthropod pests, preferred are Delphacidae; Deltocephalidae; Aphididae; Pentatomidae; *Lissorhoptrus oryzophilus, Oulema oryzae*, Pyralidae; Noctuidae, etc.

The arthropod pest control composition of the present invention may be used for controlling plant diseases such as *Thanatephorus cucumeris*.

The arthropod pest control composition of the present invention can be used in agricultural lands such as fields, paddy fields, dry fields, lawns, and orchards, or nonagricultural lands. The arthropod pest control composition of the present invention can be also used for controlling a pest in an agricultural land, etc. in which "plant", etc. is grown.

Examples of the plant to which the arthropod pest control composition of the present invention can be applied include as described below:

Crops: corn, rice, wheat, barley, rye, oat, sorghum, cotton, soybean, peanut, buckwheat, sugar beet, rapeseed, sunflower, sugar cane, tobacco, etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, rape, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweet potato, yam, aroid, etc.;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.;

Trees other than fruit trees: tea, mulberry, flowering trees (azalea, camellia, hydrangea, sasanqua, Japanese star anise, cherry, tulip tree, crape myrtle, orange osmanthus, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, spruce, elm, horse chestnut, etc.), coral tree, podocarpus, cedar, Japanese cypress, croton, *Euonymus japonicus, Photinia glabra*, etc.;

lawns: Zoysia (zoysiagrass, *Zoysia matrella*, etc.), Bermuda grasses (*Cynodon dactylon*, etc.), bent grasses (*Agrostis alba*, creeping bent grass, hiland bent, etc.), blueglasses (meadow grass, bird grass, etc.), fescue (tall fescue, chewings fescue, creeping red fescue, etc.), ryegrasses (darnel, rye grass, etc.), orchard grass, timothy grass, etc.;

Others: flowers (rose, carnation, chrysanthemum, prairie gentian, gypsophila, gerbera, marigold, salvia, petunia, verbena, tulip, aster, gentian, lily, pansy, cyclamen, orchid, convallaria, lavender, stock, ornamental cabbage, primula, poinsettia, gladiolus, cattleya, daisy, cymbidium, begonia, etc.), bio-fuel plants (Jatropha, safflower, camelina, switchgrass, Miscanthus, reed canary grass, giant reed, kenaf, cassava, willow, etc.), ornamental plants, etc.

Among the above plants, preferred are corn, wheat, rice, etc., and particularly preferred is rice.

The "plant" as used herein may be those having resistance, which is imparted by a genetic engineering technique or a cross-breeding method.

The method for controlling an arthropod pest of the present invention (hereinafter referred to as "the control method of the present invention") comprises applying an effective amount of the present amide compound, the present spinosin compound and the present compound (A) to a plant or an area in which a plant is grown. The plant as used herein include the stems and leaves of plants, the flowers of plants, the fruits of plants, the seeds of plants, etc.

In the control method of the present invention, the present amide compound, the present spinosin compound and the present compound (A) may be applied simultaneously or separately to a plant or an area in which a plant is grown, but generally the composition of the present invention comprising said compounds is applied for ease of treatment.

The "effective amount" as used herein means the total amount of the present amide compound, the present spinosin compound and the present compound (A), which is capable of exerting the controlling effect on an arthropod pest.

In the control method of the present invention, examples of the application of the present amide compound, the present spinosin compound and the present compound (A) include application to the stems and leaves of plants such as foliage application; application to the seeds of plants; and application to area in which plants are grown such as soil application and submerged application.

Specific examples of the application to the stems and leaves of plants such as foliage application in the present invention include application to the surface of cultivated plants such as ground application by using manual sprayers, power sprayers, boom sprayers or Pancle sprayers, or aerial application or spraying by using radio control helicopters, etc.

Specific examples of the application to the seeds of plants in the present invention include immersion treatment, spray coating treatment, dressing treatment, film coating treatment and pellet coating treatment.

Specific examples of the application to area in which plants are grown such as soil application and submerged application in the present invention include planting hole treatment, plant foot treatment, planting furrow treatment, planting row treatment, broadcast treatment, side row treatment, seedling box treatment, seedbed treatment, mixing with culture soil, mixing with seedbed soil, mixing with a paste fertilizer, water surface treatment, spraying on water, etc., preferably seedling box treatment.

When the arthropod pest control composition of the present invention is applied to a plant or an area in which a plant is grown, the application amount varies depending on the kinds of plant to be protected, the species or population size of arthropod pest to be controlled, the form of a formulation, the timing of application, weather conditions, etc., but is generally within a range from 0.05 to 10,000 g, preferably from 0.5 to 1,000 g per 1,000 m$^2$ of an area where a plant is grown, in terms of the total amount of the present amide compound, the present spinosin compound and the present compound (A).

When the arthropod pest control composition of the present invention is applied to a rice seedling box, the application amount is generally within a range from 0.1 to 35 g, preferably from 0.2 to 20 g per one rice seedling box (width: about 60 cm, length: about 30 cm), in terms of the total amount of the present amide compound, the present spinosin compound and the present compound (A).

When the arthropod pest control composition of the present invention is applied to 20 rice seedling boxes per 1,000 m$^2$ of an area where rice is grown after transplantation, the application amount is generally within a range from 2 to 700 g, preferably from 4 to 400 g per 1,000 m$^2$ of an area where rice is grown after transplantation, in terms of the total amount of the present amide compound, the present spinosin compound and the present compound (A).

When the arthropod pest control composition of the present invention is applied to the seeds of plants, the application amount varies depending on the kinds of plant to be protected, the species or population size of arthropod pest to be controlled, the form of a formulation, the timing of application, weather conditions, etc., but is generally within a range from 0.001 to 100 g, preferably from 0.05 to 50 g per 1 kg of the seeds, in terms of the total amount of the present amide compound, the present spinosin compound and the present compound (A).

The arthropod pest control composition of the present invention in the form of emulsifiable concentrate, wettable powder or suspension concentrate is generally applied after dilution with water. In this case, the total concentration of the present amide compound, the present spinosin compound and the present compound (A) is generally 0.00001 to 10% by weight, preferably 0.0001 to 5% by weight. The arthropod pest control composition of the present invention in the form of dusts or granules is generally applied as it is without dilution.

The arthropod pest control composition of the present invention may be applied to rice or an area in which rice is grown at the time, for example, before, during or after sowing or transplanting of rice. The timing of application may vary depending on the growing conditions of rice, the degree of occurrence of diseases, pests and weeds, weather conditions, etc., but is generally within a range from 30 days before sowing of rice to 20 days after transplanting of rice, preferably before sowing to before transplanting, more preferably 3 days before transplanting to before transplanting.

EXAMPLES

Hereinafter, the present invention will be described in more detail with reference to Formulation Examples and Test Examples, but not limited thereto. In the Examples, the term "part(s)" means part(s) by weight unless otherwise specified.

Formulation Example 1

Two (2) parts of the present amide compound, 0.5 parts of spinetoram, 1.5 parts of clothianidin, 1 part of synthesis hydrated silicon oxide, 2 parts of calcium lignosulfonate, 30 parts of bentonite and the rest parts of kaolin clay are mixed, and then 100 parts of the mixture is finely-ground and mixed. After adding water thereto, the mixture is sufficiently kneaded and then dried while grinding to obtain granules.

Formulation Examples 2 to 9

The same procedure as described in Formulation Example 1 is repeated, except that each used amount of each compound as shown in Table 1 is used instead of 1.5 parts of clothianidin, to obtain each of the target granules.

TABLE 1

| Formulation Example | Compound | Used amount [part] |
| --- | --- | --- |
| 2 | Imidacloprid | 2 |
| 3 | Thiamethoxam | 2 |
| 4 | Thiamethoxam | 8 |
| 5 | Dinotefuran | 2 |
| 6 | Fipronil | 1 |
| 7 | Pymetrozine | 3 |
| 8 | Present compound (b) | 2 |
| 9 | Present compound (b) | 4 |

Formulation Example 10

Two (2) parts of the present amide compound, 1 part of spinosad, 1.5 parts of clothianidin, 1 part of synthesis hydrated silicon oxide, 2 parts of calcium lignosulfonate, 30 parts of bentonite and the rest parts of kaolin clay are mixed, and then 100 parts of the mixture is finely-ground and mixed. After adding water thereto, the mixture is sufficiently kneaded and then dried while grinding to obtain granules.

Formulation Examples 11 to 18

The same procedure as described in Formulation Example 10 is repeated, except that each used amount of each compound as shown in Table 2 is used instead of 1.5 parts of clothianidin, to obtain each of the target granules.

TABLE 2

| Formulation Example | Compound | Used amount [part] |
| --- | --- | --- |
| 11 | Imidacloprid | 2 |
| 12 | Thiamethoxam | 2 |
| 13 | Thiamethoxam | 8 |
| 14 | Dinotefuran | 2 |
| 15 | Fipronil | 1 |
| 16 | Pymetrozine | 3 |
| 17 | Present compound (b) | 2 |
| 18 | Present compound (b) | 4 |

Formulation Example 19

Three (3) parts of the present amide compound, 15 parts of spinetoram and 15 parts of clothianidin are added to a mixture of 4 parts of sodium lauryl sulfate, 2 parts of calcium lignosulfonate, 20 parts of a fine powder of synthetic hydrated silicon oxide and 41 parts of diatomaceous earth, and then the resultant mixture is sufficiently mixed with stirring to obtain a wettable powder.

Formulation Examples 20 to 25

The same procedure as described in Formulation Example 19 is repeated, except that each used amount of each compound as shown in Table 3 is used instead of 15 parts of clothianidin, to obtain each of the target wettable powders.

TABLE 3

| Formulation Example | Compound | Used amount [part] |
| --- | --- | --- |
| 20 | Imidacloprid | 15 |
| 21 | Thiamethoxam | 15 |
| 22 | Dinotefuran | 15 |
| 23 | Fipronil | 15 |
| 24 | Pymetrozine | 15 |
| 25 | Present compound (b) | 15 |

Formulation Example 26

Three (3) parts of the present amide compound, 15 parts of spinosad and 15 parts of clothianidin are added to a mixture of 4 parts of sodium lauryl sulfate, 2 parts of calcium lignosulfonate, 20 parts of a fine powder of synthetic hydrated silicon oxide and 41 parts of diatomaceous earth, and then the resultant mixture is sufficiently mixed with stirring to obtain a wettable powder.

Formulation Examples 27 to 32

The same procedure as described in Formulation Example 26 is repeated, except that each used amount of each compound as shown in Table 4 is used instead of 15 parts of clothianidin, to obtain each of the target wettable powders.

TABLE 4

| Formulation Example | Compound | Used amount [part] |
| --- | --- | --- |
| 27 | Imidacloprid | 15 |
| 28 | Thiamethoxam | 15 |
| 29 | Dinotefuran | 15 |
| 30 | Fipronil | 15 |
| 31 | Pymetrozine | 15 |
| 32 | Present compound (b) | 15 |

Formulation Example 33

One (1) part of the present amide compound, 0.5 parts of spinetoram, 0.15 parts of clothianidin, 10 parts of talc and the rest parts of kaolin clay are finely-ground and mixed to obtain 100 parts of dusts.

Formulation Examples 34 to 40

The same procedure as described in Formulation Example 33 is repeated, except that each used amount of each compound as shown in Table 5 is used instead of 0.15 parts of clothianidin, to obtain each of the target dusts.

TABLE 5

| Formulation Example | Compound | Used amount [part] |
| --- | --- | --- |
| 34 | Clothianidin | 0.5 |
| 35 | Imidacloprid | 0.25 |
| 36 | Thiamethoxam | 0.35 |
| 37 | Dinotefuran | 0.35 |
| 38 | Fipronil | 0.25 |

TABLE 5-continued

| Formulation Example | Compound | Used amount [part] |
|---|---|---|
| 39 | Pymetrozine | 0.25 |
| 40 | Present compound (b) | 0.35 |

Formulation Example 41

One (1) part of the present amide compound, 0.5 parts of spinosad, 0.15 parts of clothianidin, 10 parts of talc and the rest parts of kaolin clay are finely-ground and mixed to obtain 100 parts of dusts.

Formulation Examples 42 to 48

The same procedure as described in Formulation Example 41 is repeated, except that each used amount of each compound as shown in Table 6 is used instead of 0.15 parts of clothianidin, to obtain each of the target dusts.

TABLE 6

| Formulation Example | Compound | Used amount [part] |
|---|---|---|
| 42 | Clothianidin | 0.5 |
| 43 | Imidacloprid | 0.25 |
| 44 | Thiamethoxam | 0.35 |
| 45 | Dinotefuran | 0.35 |
| 46 | Fipronil | 0.25 |
| 47 | Pymetrozine | 0.25 |
| 48 | Present compound (b) | 0.35 |

Formulation Example 49

Ten (10) parts of the present amide compound, 2 parts of spinetoram, 6.6 parts of clothianidin, 30 parts of white carbon containing 50 parts of ammonium polyoxyethylene alkylether sulfate and the rest parts of water are mixed, and then 100 parts of the resultant mixture is finely-ground by a wet grinding method to obtain a suspension concentrate.

Formulation Examples 50 to 56

The same procedure as described in Formulation Example 49 is repeated, except that each used amount of each compound as shown in Table 7 is used instead of 6.6 parts of clothianidin, to obtain each of the suspension concentrates.

TABLE 7

| Formulation Example | Compound | Used amount [part] |
|---|---|---|
| 50 | Imidacloprid | 8 |
| 51 | Thiamethoxam | 8 |
| 52 | Dinotefuran | 5 |
| 53 | Dinotefuran | 10 |
| 54 | Fipronil | 5 |
| 55 | Pymetrozine | 10 |
| 56 | Present compound (b) | 8 |

Formulation Example 57

Ten (10) parts of the present amide compound, 2 parts of spinosad, 6.6 parts of clothianidin, 30 parts of white carbon containing 50 parts of ammonium polyoxyethylene alkylether sulfate and the rest parts of water are mixed, and then 100 parts of the resultant mixture is finely-ground by a wet grinding method to obtain a suspension concentrate.

Formulation Examples 58 to 64

The same procedure as described in Formulation Example 57 is repeated, except that each used amount of each compound as shown in Table 8 is used instead of 6.6 parts of clothianidin, to obtain each of the suspension concentrates.

TABLE 8

| Formulation Example | Compound | Used amount [part] |
|---|---|---|
| 58 | Imidacloprid | 8 |
| 59 | Thiamethoxam | 8 |
| 60 | Dinotefuran | 5 |
| 61 | Dinotefuran | 10 |
| 62 | Fipronil | 5 |
| 63 | Pymetrozine | 10 |
| 64 | Present compound (b) | 8 |

The effects of the present invention will be demonstrated below with reference to Test Examples.

Test Example 1

Each 10 mg of the present amide compound, spinetoram, spinosad, dinotefuran and the present compound (b) was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water to a given concentration.

The water dilution of the present amide compound, the water dilution of spinetoram or spinosad, and the water dilution of dinotefuran or the present compound (b) were mixed to prepare a test solution.

Each 1 ml of the test solution was sprayed onto a soil in the vicinity of the foot of rice seedling (*Oryza sativa*, cultivar: Hinohikari) at the 2.5 leaf stage grown in a in a 200-hole plug tray. After standing for 2 hours, the seedling was transplanted to a flooded soil in 1/10,000a Wagner pot and then the pot was placed in a greenroom (night temperature: 17° C., day temperature: 22° C.) One (1) day after the treatment, 10 third-instar nymphs of *Nilaparvata lugens* were released thereto. This is called a treated-section.

In the same manner as in the treated-section, a rice seedling without any treatment with the test solution was transplanted and then the insects were released thereto. This is called an untreated-section.

Four (4) days after releasing the tested nymphs, the insects were observed for life or death. From the observation results, an insect death rate was calculated by the following Equation 1) and a corrected insect death rate was calculated by the following Equation 2). For each treatment, there were 3 replicates. The average values are shown in Table 9.

Insect death rate (%)=(Number of tested insects−number of surviving insects)/Number of tested insects×100   Equation 1);

Corrected insect death rate (%)={(Insect death rate in treated section−Insect death rate in untreated section)/(100−Insect death rate in untreated section)}×100   Equation 2);

TABLE 9

| Comp. No. | Test compound | Application amount [mg/seedling] | Corrected insect death rate [%] |
|---|---|---|---|
| 1 | Present amide compound | 1.0 | 100 |
|  | Spinetoram | 0.25 |  |
|  | Dinotefuran | 1.0 |  |
| 2 | Present amide compound | 1.0 | 97 |
|  | Spinetoram | 0.25 |  |
|  | Present compound (b) | 1.0 |  |
| 3 | Present amide compound | 1.0 | 100 |
|  | Spinosad | 0.5 |  |
|  | Dinotefuran | 1.0 |  |
| 4 | Present amide compound | 1.0 | 100 |
|  | Spinosad | 0.5 |  |
|  | Present compound (b) | 1.0 |  |

Test Example 2

Each 10 mg of the present amide compound, spinetoram, spinosad, and pymetrozine was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water to a given concentration.

The water dilution of the present amide compound, the water dilution of spinetoram or spinosad, and the water dilution of pymetrozine were mixed to prepare a test solution.

Each 1 ml of the test solutions was sprayed onto a soil in the vicinity of the foot of a rice seedling (Oryza sativa, cultivar: Hinohikari) at the 2.5 leaf stage grown in a 200-hole plug tray. After standing for 2 hours, the seedling was transplanted to a flooded soil in 1/10,000a Wagner pot and then the pot was placed in a greenroom (night temperature: 17° C., day temperature: 22° C.). Two (2) days after the treatment, the foot of the seedling was covered by a plastic cup and 10 nymphs (5 males and 5 females), which here $5^{th}$ inster of Nilaparvata lugens were released thereto. This is called a treated-section.

In the same manner as in the treated-section, a rice seedling without any treatment with the test solution was transplanted and then the insects were released thereto. This is called an untreated-section.

Five (5) days after releasing the insects, all released insects were removed. Seventeen (17) days after releasing the insects, the number of freshly-hatched nymphs parasitizing rice was examined. From the observation results, a control value was calculated by the following Equation 3). For each treatment, there were 3 replicates. The average values are shown in Table 10.

$$\text{Control value} = \{1-(\text{number of insects in treated section}/\text{number of insects in untreated section})\} \times 100 \quad \text{Equation 3)};$$

TABLE 10

| Comp. No. | Test compound | Application amount [mg/seedling] | Controlling value |
|---|---|---|---|
| 5 | Present amide compound | 1.0 | 96 |
|  | Spinetoram | 0.25 |  |
|  | Pymetrozine | 1.5 |  |
| 6 | Present amide compound | 1.0 | 97 |
|  | Spinosad | 0.5 |  |
|  | Pymetrozine | 1.5 |  |

Test Example 3

Each 10 mg of the present amide compound, spinetoram, spinosad, and the present compound (b) was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water to a given concentration.

The water dilution of the present amide compound, the water dilution of spinetoram or spinosad, and the water dilution of the present compound (b) were mixed to prepare a test solution.

Each 1 ml of the test solution was sprayed onto a soil in the vicinity of the foot of a rice seedling (Oryza sativa, cultivar: Hinohikari) at the 2.5 leaf stage grown in a 200-hole plug tray. After standing for 2 hours, the seedling was transplanted to a flooded soil in 1/10,000a Wagner pot and then the pot was placed in a greenroom (night temperature: 17° C., day temperature: 22° C.). Five (5) days after the treatment, the foot of the seedling was covered by a plastic cup and 10 first-instar nymphs of Chilo suppressalis were released thereto. This is called a treated-section.

In the same manner as in the treated-section, a rice seedling without any treatment with the test solution was transplanted and then the insects were released thereto. This is called an untreated-section.

Three (3) days after releasing the tested nymphs, the insects were observed for life or death. From the observation results, an insect death rate was calculated by the following Equation 4) and a corrected insect death rate was calculated by the following Equation 5). For each treatment, there were 3 replicates. The average values are shown in Table 11.

$$\text{Insect death rate (\%)} = (\text{Number of tested insects} - \text{number of surviving insects})/\text{Number of tested insects} \times 100 \quad \text{Equation 4)};$$

$$\text{Corrected insect death rate (\%)} = \{(\text{Insect death rate in treated section} - \text{Insect death rate in untreated section})/(100 - \text{Insect death rate in untreated section})\} \times 100 \quad \text{Equation 5)};$$

TABLE 11

| Comp. No. | Test compound | Application amount [mg/seedling] | Corrected insect death rate [%] |
|---|---|---|---|
| 7 | Present amide compound | 1.0 | 100 |
|  | Spinetoram | 0.25 |  |
|  | Present compound (b) | 1.0 |  |
| 8 | Present amide compound | 1.0 | 100 |
|  | Spinosad | 0.5 |  |
|  | Present compound (b) | 1.0 |  |

The invention claimed is:

1. An arthropod pest control composition comprising an amide compound represented by formula (a):

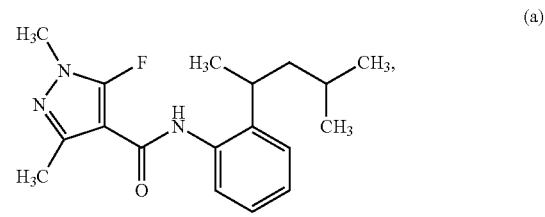 [SMILES: Cc1nn(C)c(F)c1C(=O)Nc1ccccc1C(C)CC(C)C]

spinetoram, and
one or more neonicotinoid compounds selected from the group consisting of clothianidin and imidacloprid.

2. The arthropod pest control composition according to claim 1, wherein the weight ratio of the amide compound to spinetoram is from 50:1 to 1:50.

3. The arthropod pest control composition according to claim 2, wherein the weight ratio of the amide compound to the one or more neonicotinoid compounds is from 50:1 to 1:100.

4. A method for controlling an arthropod pest, which comprises applying an effective amount of the arthropod pest control composition according to claim 1 to a plant or an area in which a plant is grown.

5. The method for controlling an arthropod pest according to claim 4, wherein the plant or the area in which a plant is grown is rice or area in which rice is grown.

6. A method for controlling an arthropod pest, which comprises applying an effective amount of the arthropod pest control composition according to claim 2 to a plant or an area in which a plant is grown.

7. The method for controlling an arthropod pest according to claim 6, wherein the plant or the area in which a plant is grown is rice or area in which rice is grown.

8. A method for controlling an arthropod pest, which comprises applying an effective amount of the arthropod pest control composition according to claim 3 to a plant or an area in which a plant is grown.

9. The method for controlling an arthropod pest according to claim 8, wherein the plant or the area in which a plant is grown is rice or area in which rice is grown.

* * * * *